United States Patent [19]

Strand

[11] Patent Number: 4,715,382

[45] Date of Patent: Dec. 29, 1987

[54] FLAT BIOMEDICAL ELECTRODE WITH REUSEABLE LEAD WIRE

[75] Inventor: Jerome E. Strand, St. Paul, Minn.

[73] Assignee: Minnesota Mining and Manufacturing Company, St. Paul, Minn.

[21] Appl. No.: 892,506

[22] Filed: Aug. 1, 1986

[51] Int. Cl.⁴ .......................... A61B 5/04; A61N 1/04
[52] U.S. Cl. ................................. 128/640; 128/798; 128/802
[58] Field of Search ........................ 128/639–641, 128/798, 802, 803

[56] References Cited

U.S. PATENT DOCUMENTS

| | | | |
|---|---|---|---|
| 3,170,459 | 2/1965 | Phipps et al. | 128/640 |
| 3,865,770 | 2/1975 | Blake | 260/27 R |
| 4,008,721 | 2/1977 | Burton | 128/802 |
| 4,067,342 | 1/1978 | Burton | 128/640 |
| 4,265,253 | 5/1981 | Abraham | 128/798 |
| 4,319,579 | 3/1982 | Cartmell | 128/640 |
| 4,353,372 | 10/1982 | Ayer | 128/640 |
| 4,409,981 | 10/1983 | Lundberg | 128/640 |
| 4,413,080 | 11/1983 | Blake | 524/187 |
| 4,458,696 | 7/1984 | Larimore | 128/798 |
| 4,524,087 | 6/1985 | Engel | 128/639 X |
| 4,539,996 | 9/1985 | Engel | 128/640 |
| 4,543,958 | 10/1985 | Cartmell | 128/640 |
| 4,554,924 | 11/1985 | Engel | 128/640 |
| 4,569,960 | 2/1986 | Blake | 524/145 |

FOREIGN PATENT DOCUMENTS 8500017  1/1985  PCT Int'l Appl. .............. 128/640

*Primary Examiner*—Lee S. Cohen
*Attorney, Agent, or Firm*—Donald M. Sell; James A. Smith; William D. Bauer

[57] ABSTRACT

A biomedical electrode (10) adapted to be applied to a body (34). The electrode (10) has a backing material (16), preferably foam, having an aperture (20). A protective web (12) at least partially secured to the backing material (16) covers the aperture (20). A removeable liner (18) is positioned between the protective web (12) and the backing material (16). An electrically conductive adhesive (28) is positioned adjacent the backing material (16) on the opposite side from the protective web (12). A second removeable release liner (30) is positioned adjacent the electrically conductive adhesive (28) opposite from the backing material (16). A lead wire (22) having a conductive portion (24) is insertable under the protective web (12) to be secured there upon the removal of the release liner (18), by the protective web (12) and the electrically conductive adhesive (28). A bottom release liner (30) may be removed and the biomedical electrode (10) may be secured to a body (34). The conductive portion (24) of the lead wire (22) should be silver or silver plated and preferably subjected to chloride treatment.

19 Claims, 3 Drawing Figures

FLAT BIOMEDICAL ELECTRODE WITH REUSEABLE LEAD WIRE

BACKGROUND OF THE INVENTION

The present invention relates generally to biomedical electrodes.

Biomedical electrodes are useful for both stimulation and body monitoring functions. Stimulation uses of biomedical electrodes include transcutaneous electronic nerve stimulation (TENS) for the treatment of pain and neuromuscular stimulation (NMS) as, for example, treatment for scoliosis. Body monitoring uses for biomedical electrodes include electrocardiogram (ECG) for monitoring heart activity.

Among biomedical electrodes in existence are those of Phipps et al, Cartmell and Larimore. Phipps et al in U.S. Pat. No. 3,170,459 discloses a biomedical instrumentation electrode constructed from multiple plies of discs made from a relatively inflexible material, i.e., cork. The electrode utilizes a conductive gel to establish contact with the body. Cartmell in U.S. Pat. No. 4,543,958 discloses a medical electrode assembly. The electrode has a flexible, dimensionally stable substrate which is striped with an electrically conductive paint. The electrode is then clamped into a bulky cable connector. Larimore in U.S. Pat. No. 4,458,696 (assigned to Minnesota Mining and Manufacturing Company) discloses a TENS electrode with a raised structure to permit entry of an attachment to a tubular electrical conductor.

These electrodes suffer from several deficiencies including that all are "high profile" electrodes and that the electrodes do not "conform" well to the body.

For monitoring electrodes electrical currents passing through the electrodes are relatively low so that excellent electrical conductivity in the electrode is required for proper performance, i.e., the ability of the biomedical electrode to pick up and transmit electrical signals obtained from the body. In most instances, good electrical performance requires that silver be utilized as a conductive element in the electrode in order to promote the proper conductivity, however, silver is an extremely expensive ingredient, the use of silver in disposable biomedical electrodes makes monitoring body functions a costly endeavor.

SUMMARY OF THE INVENTION

The present invention provides a biomedical electrode which is (1) flat and conformable to the body, (2) has excellent performance required of monitoring electrodes, (3) has a disposable body contacting portion with a reuseable electrical lead wire, and (4) is cost effective because the only silver utilized in the electrode is utilized in the reuseable lead wire.

The present invention provides a biomedical electrode which is adapted to be applied to a body. A backing material is utilized having an aperture a protective web is at least partially secured to the top side of the backing material covering the aperture. A first removeable release liner is positioned between the protective web and the backing material. An electrically conductive adhesive is positioned adjacent the bottom side of the backing material covering the aperture in the back material. A second removeable release liner is positioned adjacent the electrically conductive adhesive opposite from the backing material. A lead wire is adapted to be positioned from the top side of the backing material within the apertures so as to be adhered by the electrically conductive adhesive. This provides a biomedical electrode in which the second removeable liner may be removed and the biomedical electrode may be applied to the body with the electrically conductive adhesive. The first removeable release liner may then be removed and the lead wire may be positioned with the electrically conductive end of the lead wire within the aperture and secured by the protective web. In a preferred embodiment, the lead wire is formed with a flattened disc of electrically conductive material and, in one embodiment the flattened disc is silver plated and, in a still another embodiment, has been subjected to chloride treatment. In one embodiment, the backing material is a foam material most preferably a polyethylene foam. In another embodiment, a pressure sensitive adhesive helps to hold the protective web to the backing material.

BRIEF DESCRIPTION OF THE DRAWINGS

The foregoing advantages, construction and operation of the present invention will become more readily apparent from the following description and accompanying drawings in which.

DESCRIPTION OF THE PREFERRED EMBODIMENTS

Figure 2:
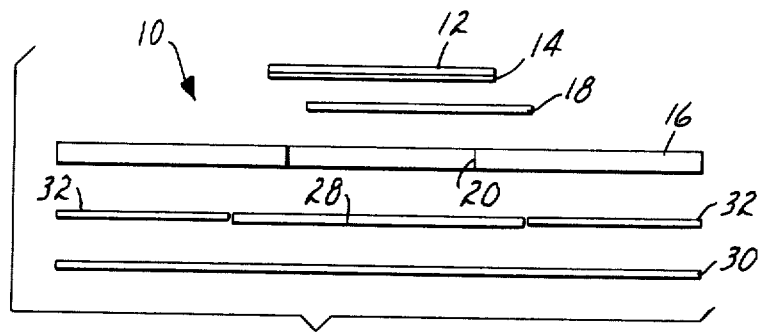
FIG. 2 is an expanded side view of the biomedical electrode.
Figure 1:
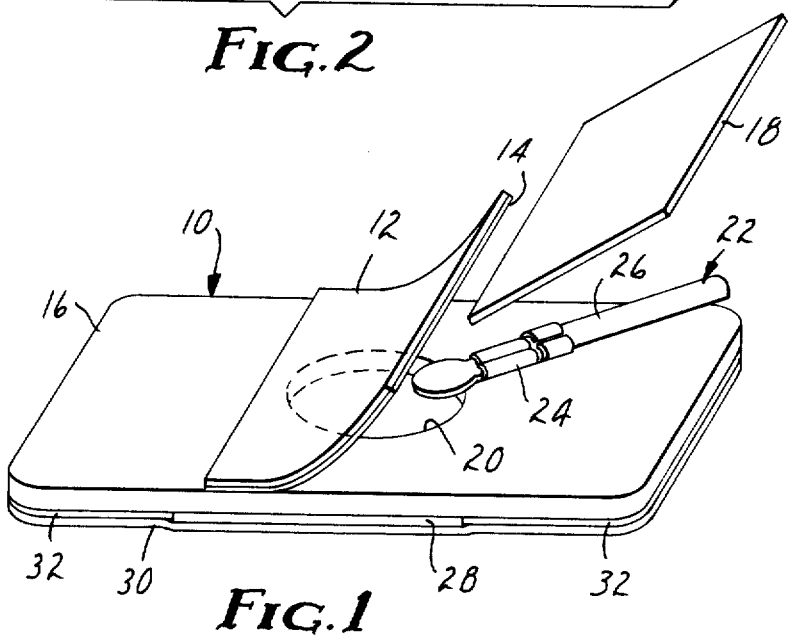
FIG. 1 is an isometric view of the biomedical electrode with the removeable release liner being removed and the electrical lead wire being inserted.

FIGS. 1 and 2 illustrate the basic construction of the biomedical electrode 10 of the present invention. A protective web 12 is applied by a pressure sensitive adhesive 14 to a backing material 16. A removeable release liner 18 is positioned between the protective web 12 and its associated pressure sensitive adhesive 14 and backing material 16. Backing material 16 contains an aperature 20 which the protective web covers. An electrical lead wire 22 having a conductive portion 24 and an insulative portion 26 is insertable into the biomedical electrode with the conductive portion 24 of lead wire 22 positioning itself within aperture of backing material 16. Although not absolutely required, it is preferred that lead wire 22 have an insulative portion 26 such that when the conductive portion of lead wire 22 is positioned within aperture 20 and covered with protective web 12 only the insulated portion 26 of lead wire 22 is exposed. An electrically conductive adhesive 28 is located on the backing material 16 below aperature 20. The electrically conductive adhesive 28 positioned in this manner will contact the conductive portion 24 of lead wire 22 when the lead wire is inserted into aperature 20. A second removeable release liner 30 is positioned below electrically conductive adhesive 28 to be removed before the biomedical electrode 10 is applied to the body. It is only necessary that electrically conductive adhesive 28 be positioned under apperature 20 in backing material 16. Electrically conductive adhesive 28, of course, could cover the entire surface area of backing material 16. If this were the case, no other adhesive in the biomedical electrode would be required. However, since electrically conductive adhesives may be more expensive than other adhesives. In a preferred embodiment, electrically conductive adhesive 28 covers only the general area of backing material 16 which is under aperture 20. Another pressure sensitive adhesive 32 is then applied to the remainder of the surface area of backing material 16 to enable the biomedical electrode to be secured to the body when it is utilized. Alternatively pressure sensitive adhesive 32 could be applied to the entire surface area of backing material 16 and the portion under aperature 20 would be removed when aperature 20 was cut into backing material 16.

Although shown in generally rectangular shape, biomedical electrode 10 by appropropriate sizing or trimming of backing material 16 may be any appropriate shape desired in order to conform or be located in any particular spot on the body. Aperture 20 is shown circular in nature and central within backing member 16 neither is absolutely required. Aperture 20 could, for example, be elongated to more appropriately conform to the conductive portion 24 of lead wire 22 and need not be centrally located within the backing material 16. As illustrated, protective web 12 covers generally only the area of backing material 16 over aperature 20. In other embodiments, protective web 12 could, of course, cover more of the surface area of backing material 16 fir the entire surface area of backing material 16, if desired.

In a preferred embodiment, protective web 12 is electrically insulative to confine the electrical signals used in the biomedical electrode 10 to the lead wire 22 or to the body. In a preferred embodiment, protective web 12 is approximately 2 mils (0.51 millimeters) thick and is preferably constructed from polyester film. Pressure sensitive adhesive 14 is preferably an acrylate adhesive. Release liner 18, which is removeable, facilitates the lifting of protective web 12 away from backing material 16 in order that lead wire 22 may be inserted and protective web 12 subsequently reapplied securing a conductive portion 24 of lead wire 22 and the biomedical electrode 10. In a preferred embodiment, release liner 18 is a Polyslick material as manufactured by James River Corporation, H. P. Smith Division, Bedford Park, Ill.

Backing material 16 may be constructed from any generally flat, body comfornable, flexible material. In a preferred embodiment, backing material 16 is a foam material, and in a more preferred embodiment is a polyethylene foam, for example, a 0.030 inches thick polyethylene foam. Lead wire 22 maybe copper wire whose insulative portion 26 is insulated with any suitable insulation, as for example, rubber or plastic. The conductive portion 24 of lead wire 22 maybe a flat crimped on conductor plate 30. Conductor plate 30 is flat which facilitates the biomedical electrode 10 being of low profile, flat and conformable to the body. In most preferred embodiments of the biomedical electrode 10, the conductive portion 24 of lead wire 22 must be silver or silver plated and preferably have a chloride treatment. Conductive adhesive 28 operates to secure the biomedical electrode 10 to the body and to provide through electrical conductivity from the body to the biomedical electrode. It is preferred that conductive adhesive 28 have better cohesion than adhesion in order to facilitate the ease with which the biomedical electrode 10 may be removed from the body. In a preferred embodiment, conductive adhesive 28 is a conductive adhesive as described in U.S. Pat. No. 4,554,924, Engel, Conductive Adhesive and Biomedical Electrode, which is hereby incorporated by reference. Removeable release liner 30 may also be Polyslick liner. Pressure sensitive adhesive 32 is also an acrylate adhesive.

Figure 3:
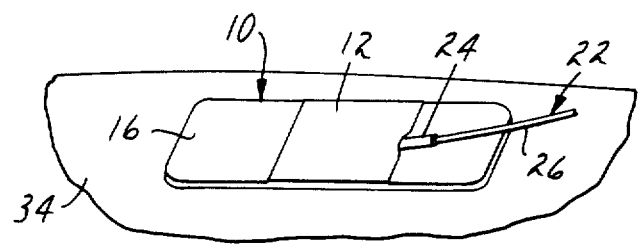
FIG. 3 is an isometric view of the biomedical electrode attached to the body.

FIG. 3 illustrates the biomedical electrode 10 having been applied to a body 34. Lead wire 22 is shown being secured in the biomedical electrode 10 by protective web 12, its associated pressure sensitive adhesive 14 (not shown) and the electrically conductive adhesive 28 (not shown) to which it contacts. Backing material 16 is secured to the body with electrically conductive adhesive 28 (not shown) and pressure sensitive adhesive 32 (not shown). When this particular use of the biomedical electrode has been completed, protective web 12 may be pulled back releasing lead wire 22 from the biomedical electrode 10 allowing the reuse of lead wire 22 and another biomedical electrode 10. Since there are no silver components to the biomedical electrode except for the silver plating or silver containment of conductive portion 24 lead wire 22 and since the lead wire 22 may be reused many times, an economical biomedical electrode 10 is provided. Biomedical electrode is flatter and more conformable to the body contours and body movement than prior art electrodes. The biomedical electrode 10 relies on adhesive contact with a flat electrical conductor as opposed to rubber connector strips or snaps. The biomedical electrode 10 has a very low profile which makes it suitable to be worn under tight clothing and to be comfortable when slept upon or when leaned against, as for example, when sitting in a chair. The biomedical electrode 10 may be trimmed to virtually any size or shape to allow flexibility and adaptability in placement and location upon the body.

Thus, it can be seen that there has been shown and described a novel, flat, biomedical electrode with a reuseable lead wire. It is to be recognized and understood, however, the various changes, modifications and substitutions in the form and of the details of the present invention can be made by those skilled in the art without departing from the scope of the invention as defined by the following claims.

What is claimed is:

1. A biomedical electrode adapted to be applied to a body, comprising:
 a backing material having an aperture, having a top side adapted to be oriented away from said body and having a bottom side adapted to be oriented toward said body;
 a protective web at least partially secured to said top side of said backing material and covering said aperture;
 a first removeable liner positioned between said protective web and said backing material, said first removeable liner covering at least a portion of the area of said backing material covered by said protective web and covering said aperture;
 an electrically conductive adhesive positioned adjacent said backing material on said bottom side of said backing material covering said aperture;
 a second removeable liner positioned adjacent said electrically conductive adhesive opposite from said backing material; and
 a lead wire having one end for being positioned within said aperture from said top side of said backing material so as to be adhered to said electrically conductive adhesive;
 whereby said second removeable liner may be removed and said biomedical electrode may be applied to said body with said electrically conductive adhesive and whereby said first removeable liner may be removed and said lead wire may be positioned with said one end within said aperture and secured by said protective web.

2. A biomedical electrode as in claim 1 wherein said one end of said lead wire is formed with a flattened disk of electrically conductive material.

3. A biomedical electrode as in claim 2 wherein said flattened disk is silver plated.

4. A biomedical electrode as in claim 3 wherein said flattened disk is a chloride treated flattened disk.

5. A biomedical electrode as in claim 1 wherein said backing material comprises a foam material.

6. A biomedical electrode as in claim 5 wherein said foam material comprises a polyethylene foam.

7. A biomedical electrode adapted to be applied to a body, comprising:
- a backing material having an aperture, having a top side adapted to be oriented away from said body and having a bottom side adapted to be oriented toward said body;
- a first layer of adhesive adjacent said top side of backing material;
- a protective web adjacent said first layer of adhesive securing said protective web to at least a portion of said tiop side of said backing material and covering said aperture;
- a first removeable liner positioned between said protective web and said backing material, said first removeable liner covering at least a portion of the area of said backing material covered by said protective web and covering said aperture;
- an electrically conductive adhesive positioned adjacent said backing material on said bottom side of said backing material covering said aperture;
- a second removeable liner positioned adjacent said electrically conductive adhesive opposite from said backing material; and
- a lead wire having one end for being positioned within said aperture from said top side of said backing material;
- whereby said second removeable liner may be removed and said biomedical electrode may be applied to said body with said electrically conductive adhesive and whereby said first removeable liner may be removed and said lead wire may be positioned with said one end within said aperture and secured by said protective web.

8. A biomedical electrode as in claim 7 wherein said one end of said lead wire is formed with a flattened disk of electrically conductive material.

9. A biomedical electrode as in claim 8 wherein said flattened disk is silver plated.

10. A biomedical electrode as in claim 9 wherein said flattened disk is a chloride treated flattened disk.

11. A biomedical electrode as in claim 7 wherein said backing material comprises a foam material.

12. A biomedical electrode as in claim 11 wherein said foam material comprises a polyethylene foam.

13. A biomedical electrode as in claim 7 wherein said first layer of adhesive comprises a pressure sensitive adhesive.

14. A biomedical electrode adapted to be electrically and mechanically attached to a lead wire and adapted to be applied to a body, comprising:
- a backing material having an aperture having a top side adapted to be oriented away from said body and having a bottom side adapted to be oriented toward said body;
- a protective web at least partially secured to said top side of said backing material and covering said aperture;
- a first removable liner positioned between said protective web and said backing material, said first removable liner covering at least a portion of the area of said backing material covered by said protective web and covering said aperture;
- an electrically conductive adhesive positioned adjacent said backing material on said bottom side of said backing material covering said aperture; and
- a second removable liner positioned adjacent said electrically conductive adhesive opposite from said backing material;
- whereby said second removable liner may be removed and said biomedical electrode may be applied to said body with said electrically conductive adhesive and whereby said first removable liner may be removed.

15. A biomedical electrode as in claim 14 wherein said backing material comprises a foam material.

16. A biomedical electrode as in claim 15 wherein said foam material comprises a polyethylene foam.

17. A biomedical electrode adapted to be electrically and mechanically connected to a lead wire and adapted to be applied to a body, comprising:
- a backing material having an aperture, having a top side adapted to be oriented away from said body and having a bottom side adapted to be oriented toward said body;
- a first layer of adhesive adjacent said top side of backing material;
- a protective web adjacent said first layer of adhesive securing said protective web to at least a portion of said top side of said backing material and covering said aperture;
- a first removable liner positioned between said protective web and said backing material, said first removable liner covering at least a portion of the area of said backing material covered by said protective web and covering said aperture;
- an electrically conductive adhesive positioned adjacent said backing material on said bottom side of said backing material covering said aperture; and
- a second removable liner positioned adjacent said electrically conductive adhesive opposite from said backing material;
- whereby said second removable liner may be removed and said biomedical electrode may be applied to said body with said electrically conductive adhesive and whereby said first removable liner may be removed.

18. A biomedical electrode as in claim 17 wherein said backing material comprises a foam material.

19. A biomedical electrode as in claim 18 wherein said foam material comprises a polyethylene foam.

* * * * *

UNITED STATES PATENT AND TRADEMARK OFFICE
CERTIFICATE OF CORRECTION

PATENT NO. : 4,715,382

DATED : December 29, 1987

INVENTOR(S) : Jerome E. Strand

It is certified that error appears in the above-identified patent and that said Letters Patent is hereby corrected as shown below:

Col. 3, line 24, "fir" should read --for--.

Col. 5, line 26, "tiop" should read --top--.

Signed and Sealed this

Fourteenth Day of June, 1988

Attest:

DONALD J. QUIGG

Attesting Officer

Commissioner of Patents and Trademarks